United States Patent
Parsons et al.

(10) Patent No.: US 6,669,981 B2
(45) Date of Patent: Dec. 30, 2003

(54) LIGHT STABILIZED ANTIMICROBIAL MATERIALS

(75) Inventors: David Parsons, Wirral (GB); Elizabeth Jacques, Chester (GB); Philip Bowler, Cheshire (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/997,545

(22) Filed: Nov. 29, 2001

(65) Prior Publication Data

US 2002/0073891 A1 Jun. 20, 2002

Related U.S. Application Data

(60) Provisional application No. 60/250,182, filed on Nov. 29, 2000.

(51) Int. Cl.[7] .......................... A61L 27/00; A61L 27/04; B05D 3/10
(52) U.S. Cl. ...................... 427/2.31; 427/2.24; 427/2.1; 427/2.25; 427/2.28; 427/2.29; 427/2.3; 427/2.31; 427/337; 427/338; 427/339
(58) Field of Search ................................ 427/2.24, 2.25, 427/2.28, 2.29, 2.3, 2.31, 337–339, 2.1

(56) References Cited

U.S. PATENT DOCUMENTS

| 4,612,337 A | * | 9/1986 | Fox et al. ................. 119/14.09 |
| 5,326,567 A | * | 7/1994 | Capelli ....................... 424/405 |
| 5,527,534 A | * | 6/1996 | Myhling ..................... 128/830 |
| 5,567,495 A | * | 10/1996 | Modak et al. ............. 428/36.9 |

FOREIGN PATENT DOCUMENTS

| WO | WO 84/01721 | 5/1994 | |
| WO | WO 01/24839 A1 | * 4/2001 | ........... A61L/15/22 |

* cited by examiner

Primary Examiner—Michael Barr
Assistant Examiner—Jennifer Kolb Michener
(74) Attorney, Agent, or Firm—John M. Kilcoyne

(57) ABSTRACT

Methods of enhancing the photostabilizing of silver in medical materials are described. More particularly, the methods increase the photostabilization of silver in certain materials comprising hydrophilic, amphoteric and anionic polymers by subjecting the polymers to solutions containing an organic solvent and silver, during or after which one or more agents are added which facilitate the photostablization of the material.

20 Claims, No Drawings

LIGHT STABILIZED ANTIMICROBIAL MATERIALS

This application claims the benefit of priority of U.S. Provisional Application No. 60/250,182, filed on Nov. 29, 2000, the entire contents of which are herein incorporated by reference.

FIELD OF THE INVENTION

This invention relates to light stabilized antimicrobial materials and methods of preparing antimicrobial polymers for use in wound dressings and medical devices.

BACKGROUND OF THE INVENTION

Infection is a problem associated with wounds. Infection can retard wound healing, is traumatic for the patient and can significantly increase treatment costs and time. Consequently there is a need to both prevent and treat infection resulting from wounds or wounds in conjunction with of wound dressings, or the use of other medical devices. Examples of such devices at increased risk include prosthetic devices, implants, or wound dressings used on acute or chronic exudating wounds. This can be achieved by the use of topical antimicrobial agents.

It is known to include antimicrobial agents in materials used in the manufacture of medical devices such as wound dressings, ostomy appliances and others. One such antimicrobial agent is silver which is used in various forms such as salts or other silver compounds and which can be used in the fibers, polymers, textiles and adhesive components used in the fabrication of such devices. A problem with silver-containing materials is that they are typically sensitive to light which causes uncontrolled discoloration of the silver-containing material. Numerous efforts have been made to render such materials photostable, however there is still a need to enhance the photostabilization of silver in certain materials comprising hydrophilic, amphoteric and anionic polymers. This is especially true where such polymers are used in medical devices. Accordingly, improved light stabilized silver-containing polymers and methods for their manufacture have been sought.

U.S. Pat. No. 5,770,255 describes methods of forming anti-microbial coatings on the surface of medical devices. The coatings described include metal ions such as silver. However, this process requires higher than ambient gas pressures and low temperatures, which are inconvenient and costly. Further this process results in a distinct disadvantage that the coating alters the dimension of the medical device. Such changes in sizes of medical devices such as implants can affect the usefulness of the product. In addition, metal ions present as coatings on the surface of medical devices such as dressings may render the product toxic.

U.S. Pat. No. 5,326,567 describes methods of making silver-containing compositions for use in medical applications. The compositions contain acrylic polyether polymers such as polyethylene glycol and are coupled with silver nitrate. However, this system is only suitable for use in solutions and is very sensitive to solvent and salt conditions. Further, this system is unlikely to be sufficiently robust to survive sterilization, which is essential for wound dressings. Additionally, this system is unsuccessful when applied to fibrous or hydrocolloid wound dressings.

U.S. Pat. No. 3,422,183 discloses the use of ultraviolet irradiated silver fluoride compositions in items such as bandages. The ultraviolet treatment reportedly enhances the activity of the silver, but the problem of photostability is not resolved. Further, this process is problematic with respect to the safety of fluoride compounds in contact with wounds, particularly using concentrations of fluoride compounds that would be required to achieve efficacy.

U.S. Pat. No. 4,646,730 discloses light stable polyvinylpyrrolidene/silver sulfadiazine (PVP/SSD) hydrogel dressings, where the gel is formed by utilizing electron beam irradiation to crosslink the PVP. Photostabilization is reportedly provided adding magnesium trisilicate to the gel, and preferably by also adding hydrogen peroxide and/or polyacrylic acid. This process requires specialized equipment to carry out the beam irradiation. Further, this process uses a hydrogel and therefore would be incompatible with other wound dressing types and technologies.

WO 00/01973 describes stabilized antimicrobial compositions containing silver for use in wound dressings. The silver is in the form of a complex with a primary, secondary or tertiary amino and the complex is associated to one or more hydrophilic polymers. However, the method of processing limits the type of products that can be produced and also alters the release rate of silver. This process is better adapted to hydrocolloid products which, due to the adhesive matrix, suffers from low availability of silver. This system is unsuitable for application to water swellable/soluble materials once they have been formulated.

U.S. Pat. Nos. 4,906,466 and 5,413,788 disclose antimicrobial compositions suitable for topical use or wound care and which exhibit suppression of light instability. The compositions comprise an antimicrobial silver compound deposited on a physiologically inert oxidic synthetic support material in particulate form, such as titanium oxide. However, the resultant product has been found be susceptible to darkening due to the reduction of the silver compound to metallic silver. Further, the use of insoluble particulates such as titanium oxide as a support is not desirable in wound healing products because the particulates are considered to be foreign bodies and must be removed.

U.S. Pat. No. 4,446,124 relates to the use of ammoniated SSD incorporated into animal tissue to prepare burn dressings. The SSD is incorporated into the tissue by soaking the tissue in an ammoniacal SSD solution or suspension. While the ammonium solution is reported to increase the concentration of silver which can be incorporated into the dressing, photostabilization is not mentioned and is unlikely. Further, this process uses animal tissue as the substrate, which is undesirable for use in wounds.

In accordance with the present invention, a novel method for the preparation of light stabilized silver-containing hydrophilic, amphoteric and anionic polymers is disclosed. This invention describes simple and inexpensive methods for the preparation of such polymers that provide effective and non toxic antimicrobial activity in a water swellable material that can be terminally sterilized.

SUMMARY OF THE INVENTION

The present invention is directed to methods of preparing a material which contains one or more hydrophilic, amphoteric or anionic polymers, where the material has antimicrobial activity. Preferably, the material containing the polymer (s) is used in a medical device, a wound dressing, or an ostomy device. Also included in the present invention are polymers and materials prepared by the methods described herein. The present invention is advantageous over the prior art because it is easily applicable to water soluble and/or water swellable materials.

In the inventive method, a solution is prepared comprising an organic solvent and a source of silver. Typically, the source of silver is initially dissolved in water, and a solution is formed by mixing water with the organic solvent. The quantity of silver should be sufficient to provide a desired silver concentration in the material. Appropriate sources of silver include silver salts, such as silver nitrate, silver chloride, silver sulphates, silver lactate, silver bromide, silver acetate silver carbonate, silver iodide, silver citrate, silver laurate, silver deoxycholate, silver salicylate, silver paraaminobenzoate, silver paraaminosalicylate, and/or mixtures thereof Other appropriate sources of silver include but are not limited to any simple water and/or alcohol soluble silver salt.

Next, the polymer is subjected to the solution for a time that is sufficient to incorporate the desired silver concentration. During or after the period wherein the polymer is subjected to the solution, the polymer is subjected to one or more agents which facilitate the binding of the silver and the polymer together. Suitable agents include ammonia, ammonium salts, thiosulphates, chlorides, and/or peroxides. In one preferred embodiment, the agent is aqueous ammonium chloride.

The resultant material is substantially photostable upon drying of the material. However, the material will dissociate to release the silver if the material is rehydrated.

DETAILED DESCRIPTION OF THE INVENTION

We have found that it is possible to stabilize silver in polymers which are used in medical-related materials. This gives the advantage that the materials exhibit anti-microbial activity while being less susceptible to photo-degradation or light-sensitivity. Such a light-stabilized medical material is particularly suitable for use in wound dressings, that create a moist wound healing environment particularly those used for moderately or heavily exuding wounds such as chronic or acute wounds. Other medical materials which benefit from the methods described herein include ostomy products, ostomy appliances, or other medical materials that are exposed to potentially infectious agents.

Accordingly, the invention provides methods of preparing a material which contains one or more hydrophilic, amphoteric or anionic polymers, wherein the polymers have anti-microbial activity. Preferably, the material containing the polymer(s) is used in a medical device, a wound dressing, or an ostomy device. Materials which are particularly adapted for the inventive method include gel-forming fibers such as Aquacel™ (WO 93/12275, WO 94/16746, WO 99/64079, and U.S. Pat. No. 5,731,083), orthose described in WO 00/01425 or PCT/GB 01/03147; wound dressings containing similar gel-forming fibers behind or overlying a non-continuous or perforated skin-contact layer such as Versiva™ (U.S. Pat. No. 5,681,579, WO 97/07758 and WO 00/41661); DuoDerm™ (U.S. Pat. No. 4,538,603), DuoDerm CGF™ (U.S. Pat. No. 4,551,490 and EP 92 999), or a blend of two or more fibres such as Carboflex™ (WO 95/19795). The present invention well-suited for other materials which contain carboxymethylcellulose. Further, the present invention is advantageous over the prior art because it is easily applicable to water soluble and/or water swellable materials.

Polymers suitable for the present invention include, but are not limited to, polysaccharides or modified polysaccharides, polyvinylpyrrolidone, polyvinyl alcohols, polyvinyl ethers, polyurethanes, polyacrylates, polyacrylamides, collagen, gelatin, or mixtures thereof. In preferred embodiments, the polymers contain carboxymethylcellulose (CMC) such as sodium CMC. In one embodiment, the polymer can be a polysaccharide comprising a carboxymethylcellulose or alginate, or a mixture of carboxymethylcellulose and alginate. In other embodiments, the polymers contain gel-forming fibers comprising sodium CMC, and which can be incorporated into wound dressings such as Aquacel™ (ConvaTec, Skillman, N.J.).

In the inventive method, a solution is prepared comprising an organic solvent and a source of silver. The solution should be prepared in a quantity sufficient to provide the desired silver concentration in the resulting product. The polymer is then subjected to the solvent/silver solution so as to incorporate the silver into the polymer. The treated polymer is subjected to one or more agents such that the silver-containing material is made photostable, and further where the silver will thereafter dissociate upon rehydration of the material.

The organic solvent can be any known solvent. Examples of appropriate solvents include but are not limited to industrial methylated spirit (IMS, principally ethanol), ethanol, methanol, acetone and isopropyl alcohol.

The source of the silver can be any convenient source. Examples of appropriate sources of silver include silver salts, such as silver nitrate, silver chloride, silver sulphates, silver lactate, silver bromide, silver acetate silver carbonate, silver iodide, silver citrate, silver laurate, silver deoxycholate, silver salicylate, silver paraaminobenzoate, silver paraaminosalicylate and/or mixtures thereof Other appropriate sources of silver include but are not limited to any simple water and/or alcohol soluble silver salt.

The quantity of silver should be sufficient to provide a desired silver concentration in the material. The final concentration of silver in the material is between about 0.1% and 20% by weight, for example, by weight of the resultant medical dressing. In some embodiments, the concentration of silver is between 0.1–10%, 1–10%, 10–20%, 5–20%, 5–10% or 0.1–1%. In one preferred embodiment, the final concentration of silver is between about 1 and 5% by weight of the dressing. Preferably, the concentration in the treatment solution is from 0.001 g/g of polymer to 0.2 g/g of polymer, more preferably from 0.01 g/g of polymer to 0.05 g/g of polymer. Preferably, where the source of silver is most facilely initially dissolved in water rather than the neat organic solvent, then added in an appropriate amount to give the desired concentration of silver in the final weight of polymer.

Water can be used in the present invention, especially for the purposes of initial solubilization of silver before addition of the silver to the organic solvent. The amount of water should be sufficient such that the silver is adequately dissolved in solution, but not so much to result in hydration of the polymer. While excess amounts of silver can be present in suspension, for example forming a reserve, amounts effective for incorporation into the polymer should be in solution. Such amounts would be easily determinable to those of ordinary skill in the art without undue experimentation. However, the amount of water used is no greater than 50/50 w/w of water to alcohol.

The length of time that the material is subjected to the solution is a period sufficient to incorporate the desired silver concentration into the polymer. Preferably, the material is subjected to the solution between 1 and 120 minutes. In some embodiments, the incubation time is between 1 and 60 minutes. In other embodiments, the incubation time is between 15 and 45 minutes. In still other embodiments, the incubation time is between 10–60, 10–45, 15–30, 5–15 or 10–20 minutes. Generally, the length of time necessary to subject the material to the solution will depend on the material used and can be easily determined by one of ordinary skill in the art.

Temperatures between 0 to 100° C. are appropriate for the present invention but preferably ambient temperatures are used. Different temperatures can be used at different stages within the range stated.

During or after the period wherein the polymer is subjected to the solution, it is subjected to one or more agents which facilitate photostabilization. Suitable agents include ammonia, ammonium salts, thiosulphates, chlorides, and/or peroxides. Preferred agents are ammonium salts such as ammonium chloride, ammonium acetate, ammonium carbonate, ammonium sulphate and metal halides such as sodium, potassium, calcium, magnesium and zinc chlorides. The agents can optionally include mixtures of the above salts. In one preferred embodiment, the agent is added to the treatment mixture as aqueous ammonium salt solution such as ammonium chloride, or is added separately.

The quantity of agent used will depend on the amount of polymer-containing material being prepared and the total volume of solution. Preferably, the agent is present in a concentration between 0.01 and 50% of the total volume of treatment. In some embodiments, the concentration of agent is between 0.01–25%, 0.01–10%, 0.01–5%, 0.1–5%, 0.1–25%, 0.1–10%, 1–25%, 1–10%, 1–5%, 5–25%, 10–25% or 25–50% of the total volume of treatment.

Once the facilitating agent is applied, treatment is continued for another period of time, e.g., an additional 5–30 minutes, or for a time sufficient to allow photostabilization to occur.

It is also an important aspect of the present invention that the silver is dissolved in an organic solvent to solubilize the silver salt and prevent hydration of the polymer. The silver salt can be added directly to the solvent and stirred gently until dissolved. The photostabilizing step of the process can either follow the silver-loading step or can be initiated during the course of the silver-loading step.

In addition to the articles mentioned herein, the present invention is suitable for use in medical articles such as wound dressings and skin care products.

By the term "loading" herein, is meant, ionic exchange of the cation to the polymer with silver ions.

The term, "photostable" for purposes of the present invention is meant, Controlled colour change to a desired colour with minimal change thereafter.

"Binding" as meant in the present invention, refers to the formation of a photostable compound.

The resultant polymeric material is substantially photostable upon drying. However, the material will dissociate to release the silver if the material is rehydrated.

In an exemplary process, an Aquacel™ wound dressing (e.g. 20 g), commercially available from ConvaTec, can be placed in, e.g., 127.5 ml of IMS/water (77.5:50 v/v). A silver nitrate solution is prepared, for example, with water and silver nitrate in concentrations to provide the desired final concentrations of silver in the Aquacel™ dressing (e.g., 0.0316 g/mL in water, with 10 mL added to the IMS/water solution). Final concentrations of silver in the dressings can range between 0.1% and 20% by weight of the dressing. Preferably these concentrations are between 1 and 5%. The dressing is subjected to the IMS/silver nitrate for a desired time, e.g., 15–45 minutes. Preferably after this silver treatment, sodium chloride in a concentration between 0.01 and 50% (preferably between 1 and 10%) is added to the IMS/silver nitrate bath and treatment is continued for another period of time, e.g., an additional 5–30 minutes.

Aquacel™ wound dressings having between 1 and 5% by dressing weight of silver have been found to be photostable and possess excellent anti-microbial activity. Further, irradiation does not adversely affect such silver dressings.

All publications and references, including but not limited to patents and patent applications, cited in this specification are herein incorporated by reference in their entirety as if each individual publication or reference were specifically and individually indicated to be incorporated by reference herein as being fully set forth.

What is claimed is:

1. A method of preparing a light stabilized antimicrobial material comprising the steps of
    a) preparing a solution comprising an organic solvent and a source of silver in a quantity sufficient to provide a desired silver concentration in the light stabilized antimicrobial material;
    b) subjecting a polymer to the solution for a time sufficient to incorporate the desired silver concentration into the polymer, wherein the polymer is selected from the group consisting of a polysaccharide, a modified polysaccharide, a polyvinylpyrrolidone, a polyvinyl alcohol, a polyvinyl ether, a polyurethane, a polyacrylate, a polyacrylamide, a collagen, a gelatin, and a mixture thereof; and
    c) subjecting the polymer, during or after step (b), to one or more agents which facilitate the binding of the silver on the polymer;
    wherein the silver is substantially photostable in the light stabilized antimicrobial material when dry, but will dissociate from the light stabilized antimicrobial material upon hydration of the light stabilized antimicrobial material.

2. The method of claim 1, further comprising:
    d) using the light stabilized antimicrobial material in a medical device.

3. The method of claim 1, further comprising:
    d) using the light stabilized antimicrobial material in a wound dressing.

4. The method of claim 1, further comprising:
    d) using the light stabilized antimicrobial material in an ostomy device.

5. The method of claim 1, wherein the source of silver comprises a silver salt.

6. The method of claim 5, wherein the silver salt is selected from the group consisting of silver nitrate, silver chloride, silver sulphate, silver lactate, silver bromide, silver acetate and mixtures thereof.

7. The method of claim 1, wherein the one or more agents is selected from the group consisting of ammonium salts, thiosulphates, chlorides and peroxides.

8. The method of claim 7, wherein the one or more agents is a metal halide.

9. The method of claim 7, wherein the one or more agents comprises an ammonium salt selected from ammonium chloride, ammonium acetate, ammonium carbonate, ammonium sulphate and mixtures thereof.

10. The method of claim 1, wherein the polysaccharide comprises a carboxymethylcellulose, an alginate, or a mixture thereof.

11. The method of claim 1, wherein the organic solvent is selected from the group consisting of industrial methylated spirit, denatured ethanol, methanol, acetone, isopropyl alcohol and ethanol.

12. The method of claim 1, wherein the desired silver concentration is between 0.1 and 20 wt %.

13. The method of claim 1, wherein the desired silver concentration is between 1 and 20 wt %.

14. The method of claim 1, wherein the time sufficient to incorporate the desired silver concentration into the polymer is between 1 and 120 minutes.

15. The method of claim 1, wherein the time sufficient to incorporate the desired silver concentration into the polymer is between 1 and 60 minutes.

16. The method of claim 1, wherein the polymer in step (c) is subjected to the one or more agents for 5 to 30 minutes.

17. A method of preparing a light stabilized antimicrobial material comprising the steps of a) preparing a solution comprising an organic solvent and a source of silver in a quantity sufficient to provide a desired silver concentration in the light stabilized antimicrobial material;

b) subjecting a polymer to the solution for a time sufficient to incorporate the desired silver concentration into the polymer; and c) subjecting the polymer, after step (b), to one or more agents which facilitate the binding of the silver on the polymer;

wherein the silver is substantially photostable in the light stabilized antimicrobial material when dry, but will dissociate from the light stabilized antimicrobial material upon hydration of the light stabilized antimicrobial material.

18. The method of claim 17, further comprising:

d) using the light stabilized antimicrobial material in a medical device.

19. The method of claim 17, further comprising:

d) using the light stabilized antimicrobial material in a wound dressing.

20. The method of claim 17, wherein the polymer comprises a carboxymethylcellulose, an alginate, or a mixture thereof.

* * * * *